United States Patent
Yoshida

(10) Patent No.: US 8,746,239 B2
(45) Date of Patent: Jun. 10, 2014

(54) EXTENDABLE LIGHTED INTUBATION STYLET

(76) Inventor: Douglas K. Yoshida, San Francisco, CA (US)

( * ) Notice: Subject to any disclaimer, the term of this patent is extended or adjusted under 35 U.S.C. 154(b) by 1714 days.

(21) Appl. No.: 11/879,988

(22) Filed: Jul. 18, 2007

(65) Prior Publication Data

US 2008/0017195 A1    Jan. 24, 2008

Related U.S. Application Data

(60) Provisional application No. 60/831,825, filed on Jul. 19, 2006.

(51) Int. Cl.
*A61B 1/267* (2006.01)
*A61M 16/00* (2006.01)

(52) U.S. Cl.
USPC .................. 128/200.26; 128/207.14; 600/199

(58) Field of Classification Search
USPC ............ 128/200.24, 200.26, 207.14, 207.15; 600/120, 121, 124, 178–180, 193, 196, 600/199; 200/252, 541; 362/203–206; 606/108, 106, 13–19; 607/80, 92–94, 607/124, 133, 134; 294/65.5, 190
See application file for complete search history.

(56) References Cited

U.S. PATENT DOCUMENTS

| | | | |
|---|---|---|---|
| 229,633 A | 7/1880 | Pfarre | 606/197 |
| 2,463,149 A | 3/1949 | Caine | 128/200.26 |
| 3,314,431 A | 4/1967 | Smith et al. | 128/200.26 |
| 3,754,554 A * | 8/1973 | Felbarg | 128/200.26 |
| 3,802,440 A | 4/1974 | Salem et al. | 128/205 |
| 3,957,055 A | 5/1976 | Linder et al. | 128/200.26 |
| 3,996,939 A | 12/1976 | Sheridan et al. | 128/351 |
| 4,672,960 A | 6/1987 | Frankel | 128/200.26 |
| 4,865,586 A | 9/1989 | Hedberg | 604/93 |
| 4,892,095 A | 1/1990 | Nakhgevany | 128/207.14 |
| 5,058,577 A * | 10/1991 | Six | 128/200.26 |
| 5,235,970 A | 8/1993 | Augustine | 128/200.26 |
| 5,259,371 A | 11/1993 | Tonrey | 128/200.26 |
| 5,263,478 A | 11/1993 | Davis | 128/207.14 |
| 5,269,769 A * | 12/1993 | Dhara et al. | 604/264 |
| 5,279,610 A * | 1/1994 | Park et al. | 606/108 |
| 5,337,735 A | 8/1994 | Salerno | 128/11 |
| 5,394,865 A | 3/1995 | Salerno | 128/11 |
| 5,580,147 A | 12/1996 | Salerno | 362/32 |
| 5,647,623 A * | 7/1997 | Shiao | 294/65.5 |
| RE35,595 E | 8/1997 | Six | 128/200.26 |
| 5,672,179 A | 9/1997 | Garth et al. | 606/108 |
| 5,733,242 A * | 3/1998 | Rayburn et al. | 600/120 |
| 5,749,357 A * | 5/1998 | Linder | 128/200.26 |
| 5,791,338 A | 8/1998 | Merchant | 128/200.26 |

(Continued)

*Primary Examiner* — Justine Yu
*Assistant Examiner* — Valerie L Skorupa
(74) *Attorney, Agent, or Firm* — Imperium Patent Works

(57) ABSTRACT

An extendable lighted intubation stylet enables a clinician or emergency medical personnel to introduce a breathing tube into a person's trachea. The extendable lighted intubation stylet includes a handle, a switch, a sheath, an extension member, and a light source. The extension member can be extended or retracted relative to the sheath thereby increasing or decreasing the length of the extendable lighted intubation stylet. The light source provides for superior visualization of the airway compared to a standard laryngoscope bulb. In its extended configuration, the extendable intubation stylet is immediately available in the case of an unanticipated difficult airway and can be used as a bougie. The extendable stylet is lightweight and convenient because it can be folded and placed in a pocket or in a space critical location such as a field kit or portable airway bag.

2 Claims, 20 Drawing Sheets

(56) References Cited

U.S. PATENT DOCUMENTS

| | | | |
|---|---|---|---|
| 5,819,727 A | 10/1998 | Linder | 128/200.06 |
| 5,910,105 A * | 6/1999 | Swain et al. | 600/131 |
| 5,919,183 A | 7/1999 | Field | 604/530 |
| 5,975,712 A * | 11/1999 | Shiao | 362/120 |
| 6,004,263 A * | 12/1999 | Nakaichi et al. | 600/176 |
| 6,463,927 B1 | 10/2002 | Pagan | 128/200.26 |
| 6,755,794 B2 * | 6/2004 | Soukup | 600/585 |
| 6,854,859 B2 * | 2/2005 | Cooper et al. | 362/139 |
| 6,860,264 B2 * | 3/2005 | Christopher | 128/200.26 |
| 2004/0215061 A1 * | 10/2004 | Kimmel et al. | 600/179 |
| 2005/0076914 A1 * | 4/2005 | Besharim et al. | 128/207.14 |
| 2006/0149129 A1 * | 7/2006 | Watts et al. | 600/113 |
| 2006/0247497 A1 * | 11/2006 | Gardner | 600/188 |
| 2007/0227543 A1 * | 10/2007 | Peichel | 128/207.14 |

* cited by examiner

EXTENDABLE LIGHTED INTUBATION STYLET

CROSS REFERENCE TO RELATED APPLICATION

This application is based on and hereby claims the benefit under 35 U.S.C. §119 from U.S. Provisional Application No. 60/831,825, entitled "Extendable Lighted Intubation Stylet," filed on Jul. 19, 2006, the subject matter of which is incorporated herein by reference.

BACKGROUND INFORMATION

In the course of medical care, healthcare providers often have to place an endotracheal tube into a person's airway. This process, intubation, may be necessary for artificial ventilation, protecting the airway from aspiration of stomach contents or for the delivery of anesthetics. Intubation may be performed by paramedics or military personnel in the field, in emergency departments, hospitals or in the operating room.

An endotracheal tube 34 is shown in FIG. 1. An endotracheal tube has a tubular shaft 17 with a distal end 14, a proximal end 15, an inflatable cuff 12 and an inflation lumen 10. During intubation the distal end 14 of the endotracheal tube is inserted into a person's mouth and slidably positioned into the person's trachea such that proximal end 15 projects outward from person's mouth. Inflatable cuff 12 is then used to secure the endotracheal tube 34 in the trachea. Inflatable cuff 12 is inflated by supplying air at inflation lumen 10. Oxygen and/or anesthetics are then supplied to the person by supplying them utilizing proximal end 15 of endotracheal tube 34.

In many situations a person's glottis is not visible to the physician such as when obstructed by blood, secretions, swelling, abnormal anatomy, or when person is obese. This is termed the "difficult airway" and in these situations proper intubation may be difficult and ventilation of the person may fail if endotracheal tube 34 of FIG. 1 is incorrectly inserted into the person's esophagus rather than the person's trachea. To facilitate proper intubation, a variety of introducers are utilized.

FIG. 2 is a drawing of a standard stylet 30. To facilitate intubation of the person, a plastic coated metal stylet is frequently used to stiffen endotracheal tube 34 of FIG. 1 by inserting standard stylet 30 within the endotracheal tube. A distal end 24 of standard stylet 30 is inserted into the endotracheal tube such that a proximal end 20 of the standard stylet 30 extends outward from proximal end 15 of endotracheal tube 34 of FIG. 1. The standard stylet 30, together with the endotracheal tube can then be bent to form a shape that facilitates insertion into the trachea of a person.

FIG. 3 shows a standard stylet 30 placed within an endotracheal tube 34 and disposed within a person's airway. The distal end of the endotracheal tube is disposed within a person's trachea 32. Once an endotracheal tube 34 containing standard stylet 30 is properly positioned as indicated in FIG. 3, standard stylet 30 is then removed leaving endotracheal tube 34 disposed in the trachea. A source of oxygen can then be coupled to the proximal end of endotracheal tube 34.

Since visibility is often partially or fully obstructed in the case of a difficult airway, intubation utilizing a standard stylet is not optimal. The distal end 14 of endotracheal tube 34 of FIG. 1 is many millimeters in diameter and decreases the operator's visibility of the airway. The large diameter of endotracheal tube 34 makes it difficult to slip under the epiglottis such to access to the trachea. Therefore, since visibility is not optimal and since the relatively large diameter of the endotracheal tube further frustrates intubation, other devices or introducers are often utilized in the difficult airway situation.

One of these introducers is shown in FIG. 4, a drawing of a gum elastic bougie 40 or "bougie." The bougie 40 is used in combination with a laryngoscope to first locate a person's epiglottis or vocal cords and then as a guide for insertion of the endotracheal tube.

The bougie 40 is approximately 70 centimeters long and includes a distal end 44 and a proximal end 42. Both the proximal end 42 and distal end 44 are rounded such for prevention of trauma to the person during insertion of bougie 40 into the airway. Commercially supplied bougies are marketed and sold in varying diameters, and some are approximately 5 millimeters in diameter. This relatively small diameter of the bougie compared to the diameter of an endotracheal tube increases the possibility of proper insertion since it fits into smaller openings and allows for increase visibility during intubation. However, the bougie is approximately 70 centimeters in length and is cumbersome and is also not immediately disposed to operator's use.

FIG. 5 shows a bougie 40 disposed within a person's airway. When bougie 40 is correctly guided into the airway, distal end 44 will enter a person's trachea 32. The trachea 32 is composed of C-shaped cartilaginous rings known as tracheal rings 39. An esophagus 57 is devoid of tracheal rings and is shown in FIG. 5 adjacent trachea 32. During intubation, distal end 44 of bougie 40 glides over tracheal rings 39 and the physician or operator will feel a vibration or tapping sensation at a proximal end 42. This is known as "tracheal clicking." The operator is then assured that bougie 40 is correctly located in the airway and not in the person's esophagus. If tracheal clicking is not felt at proximal end 42, bougie 40 is likely disposed within esophagus 57 and must be withdrawn and replaced.

Bougie 40 finds use in the difficult airway situation since it is smaller in diameter than the endotracheal tube and allows for greater operator visibility and since distal end 44 is easier to slip under the epiglottis and into the airway when compared to the endotracheal tube. Bougie 40 is also manufactured with an angled or "Coude tip" which facilitates tracheal clicking as a result of improved contact with tracheal rings 39.

Once the bougie has been correctly placed within the person's trachea, endotracheal tube 34 can be inserted over the proximal end 42 of bougie 40 and slidably positioned into the person's trachea using bougie 40 as a guide. Bougie 40 is then slidably removed from the person leaving endotracheal tube 34 disposed within the trachea for ventilation or delivery of anesthetics. Although a bougie may offer improved performance over the standard stylet, there remains a need for improved visibility and bougie 40 is also prone to twisting during use making proper handling less than ideal.

Another introducer, a lightwand 60, is shown in FIG. 6. The lightwand has a handle 52 located at the proximal end of a shaft 54 and a light source 56 located at the distal end of shaft 54. A switch 58 disposed on handle 52 of lightwand 60 and allows the operator to control light source 56.

To intubate a person using a lightwand, an endotracheal tube is slipped over the light source 56 at the distal end of shaft 54 and is positioned on shaft 54 between handle 52 and light source 56. A bend is then placed at the distal portion of the light wand such that the distal end containing light source 56 is at an approximate 90 degree angle relative to the axis of shaft 54. The light source is then switched on using switch 58 and the distal portion of the lightwand is then inserted into person's throat and advanced until an external glow is seen emanating from the person's suprasternal notch. This glow is externally visible to the operator and indicates that the lightwand is properly positioned in the trachea of a person. If a glow is not seen than the lightwand is incorrectly positioned in person's esophagus and must be withdrawn and reinserted until proper placement is achieved.

FIG. 7 shows a lightwand 60 and an endotracheal tube 34 disposed within a person's trachea. A light source 56 is viewable externally when lightwand 60 is properly positioned in the airway as shown. If lightwand 60 were incorrectly positioned within an esophagus 57, light source 56 would not be externally visible. Lightwand 60 is smaller than other introducers such as a bougie and can easily store in situations where space is limited such as a field kit or portable airway bag. However lightwand 60 is not adaptable to standard orotracheal techniques since it calls for the use of a guide or a metal stylet that is removable such to prevent trauma. Additionally, lightwands do not produce the tracheal clicking as evidence of proper intubation thus depriving the operator of an effective manner of validating proper placement.

In a trauma situation, the aforementioned introducers and similar commercially available devices are problematic since they are either quite lengthy, cumbersome or not readily adaptable to standard orotracheal techniques. In addition, where one introducer may have been initially selected to intubate a person, if physician subsequently desires a different introducer, he will waste precious time as he must remove the introducer that was initially selected and replace it with the more desirable alternative. An optimal introducer is thus desired which eliminates the combined disadvantages of the aforementioned introducers.

SUMMARY

An extendable lighted intubation stylet has been invented to enable a clinician or emergency medical personnel to easily introduce a breathing tube into a person's trachea. The extendable lighted intubation stylet includes a sheath member, an extension member and a light source.

The extension member can be extended or retracted relative to the sheath such to increase or decrease the length of the extendable lighted intubation stylet. When utilized in retracted form, the extendable stylet is compact and may be used as a replacement for the standard stylet for routine intubations. The light source of the extendable lighted intubation stylet provides for superior visualization of the airway compared to a standard laryngoscope bulb. In extended configuration, the extendable intubation stylet is immediately available in the case of the unanticipated difficult airway and the need to look for another device in this time critical period is obviated. The extension member can be quickly extended similar to a bougie. It is then retractable in the case where the practitioner decides to use it as a bougie and then as a standard stylet or a lightwand. The extension member contains a stiffening wire and can be bent at a 90 degree or a preferred angle when in use as a lightwand. The extendable lighted intubation stylet is compact and is thus ideal for pre-hospital use such as by paramedics or in military use. It can be folded and placed in a pocket or in space critical locations such as a field kits or portable airway bags.

When used similar to a bougie, the distal end containing the light source will be placed under a person's epiglottis and advanced. As the light source passes into the trachea the operator will first see light emanating from person's suprasternal notch. Upon further advancement of the extendable stylet the operator will then experience vibratory sensations from the distal end of the extendable stylet bumping the cartilaginous rings of the trachea indicating that the stylet is properly positioned in the trachea.

When used in this manner, the operator has two indications that the extendable stylet is correctly positioned in the airway, the light seen externally at person's suprasternal notch and the vibratory sensations produced by the distal end of the extendable stylet bumping into the cartilaginous tracheal rings.

If this is not successful, the extension member can be quickly retracted and the device may be used similar to a lightwand. When used similar to a lightwand, light from the light source will be seen externally at person's suprasternal notch indicating that the extendable stylet is properly positioned in the trachea and not in the person's esophagus. If a glow is not seen then the extendable stylet is in the esophagus and must be repositioned.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Figure 8:
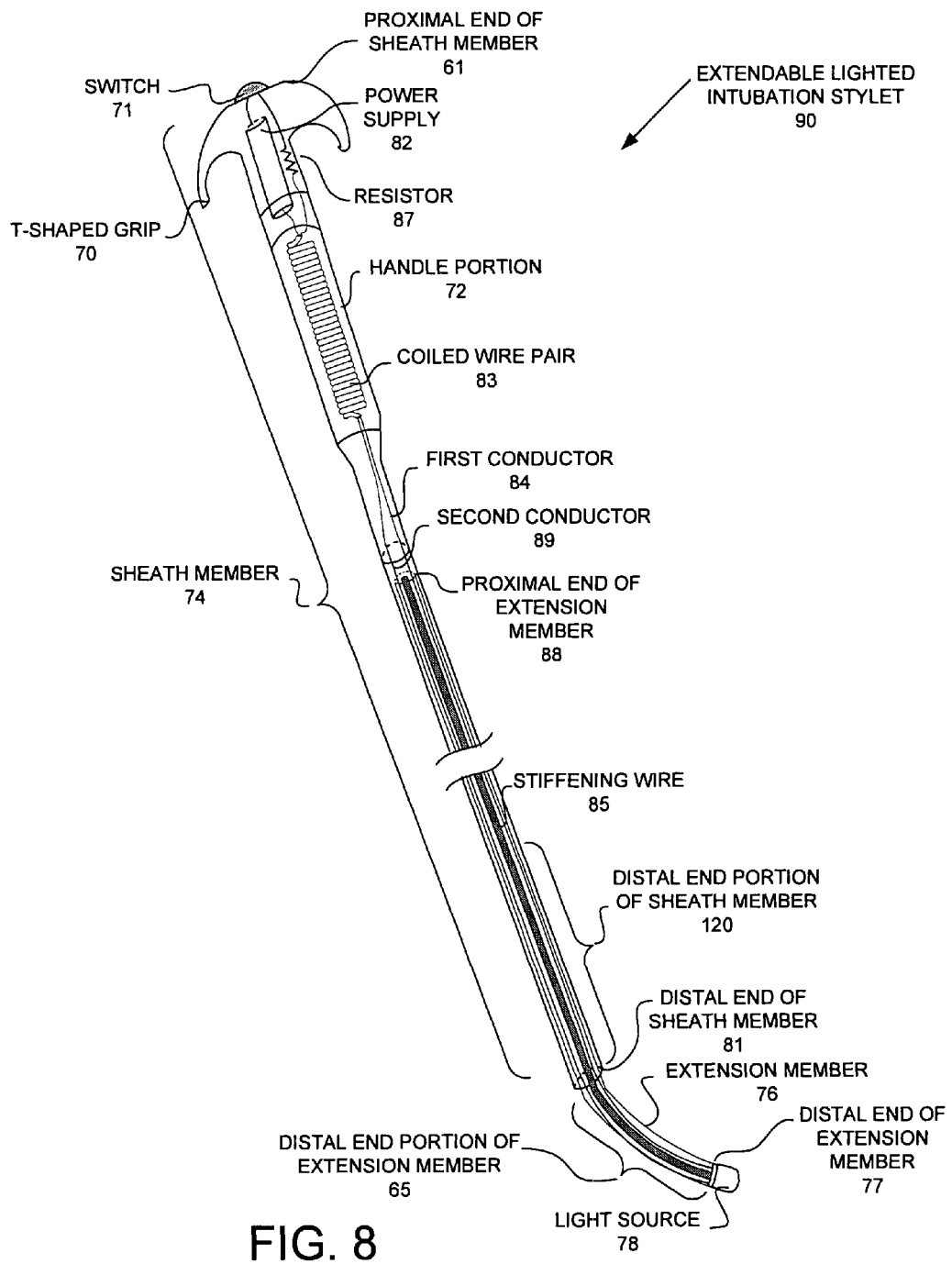
FIG. 8 is a cross sectional side elevation drawing of an extendable lighted intubation stylet. The extendable lighted intubation stylet is shown in its fully retracted position.

FIG. 8 is a drawing of an extendable lighted intubation stylet 90 in accordance with one novel aspect. Extendable lighted intubation stylet 90 includes a sheath member 74, an extension member 76, and a light source 78. In one embodiment, light source 78 is a light emitting diode (LED).

Sheath member 74 has a proximal end 61, a tube section, a distal end portion 120, and a distal end 81. Sheath member 74 also has a handle portion 72 which is coupled to a T-shaped grip 70 at proximal end 61 of sheath member 74. Extension member 76 is slidably coupled to sheath member 74 and has a proximal end 88, a distal end portion 65, and a distal end 77. Light source 78 is disposed upon the distal end portion 65.

Also shown in this FIG. 8 is a power supply 82. The positive terminal of power supply 82 is connected to one terminal of a switch 71. The opposite terminal of switch 71 is connected to a terminal of a resistor 87. The opposite terminal of resistor 87 is connected to one of two insulated wires within a coiled wire pair 83 which is further connected to a first conductor 84. First conductor 84 then extends to the positive terminal of light source 78. The negative terminal of power supply 82 is connected to the second of the two insulated wires within coiled wire pair 83 which further connects to a second conductor 89 which in turn further connects to the negative terminal of light source 78. Power supply 82 can be batteries disposed in series such to provide at least 3.6 Volts to light source 78. In other embodiments, power supply 82 is a single 6 Volt medical battery.

A stiffening wire 85 is disposed within extension member 76 and permits the distal end portion of extension member 76 to be more formable than sheath member 74.

It is desirable that the extendable lighted stylet is disposable after a single use and therefore be made of inexpensive materials and is easily manufactured. The extension member should be flexible to eliminate it as a source of trauma during intubation but must be of sufficient stiffness to permit an operator to locate the airway and facilitate insertion.

The hardness of plastics and similar material is measured by a Shore or durometer test and is often used as a proxy for flexibility (flexural modulus). Extension member 76 may be made from aliphatic polyurethane of varying hardness although generally the range of 50 Shore A to 90 Shore D is satisfactory. Sheath member 74 and extension member 76 are hollow and the material is selected such to increase the hardness. Materials that create a hardness of approximately 90 Shore D are used in embodiments wherein both sheath 74 and extension member 76 are tubular. Additional materials that could yield the desired degree of both rigidity and flexibility include polyvinyl chloride (PVC) materials, gum elastic materials, polyurethane materials, polyethylene materials, fluorinated hydrocarbon polymer materials, polytetrafluoroethylene (PTFE) materials, silicone rubber materials, nylon materials, flexible silicone compositions, polyamide materials, and polyester block amide materials.

The desired stiffness of the extension member 76 is about 20-50 MPa as measured with a Tinius Olsen stiffness tester.

Sheath 74 is approximately 4 millimeters to 5.5 millimeters in diameter and is sized to fit within endotracheal tubes of standard sizes. The length of sheath 74 is approximately 40 centimeters to 60 centimeters. Extension member 76 is approximately 10 centimeters to 40 centimeters in length. The small diameter of extension member 76 provides for greater visibility when intubating persons and can be easily inserted under the epiglottis.

Light source 78 can be a light emitting diode "LED" and is used as supplementary light to the standard laryngoscope bulb. The light is also usable to indicate the correct placement of the extendable stylet in the airway when the extendable stylet is being used as a lightwand.

In this FIG. 8, extension member 76 is shown in its retracted position relative to sheath 74. In this configuration, the overall length of the extendable stylet is approximately 50 centimeters. In the retracted position, the extendable stylet can be operated as either a lightwand or as a standard stylet. Extension member is 10 centimeters to forty centimeters in length.

The handle portion 72 of sheath member 74 is coupled to a T-shaped grip 70. T-shaped grip 70 allows the operator to control the axial rotation of the extendable stylet. This design eliminates unintended axial rotation of the inducer thus eliminating the potential for the extendable stylet to cause trauma.

Stiffening wire 85 is disposed within extension member 76 from a proximal end 88 of extension member 76 to a distal end 77 of extension member 76. The stiffening wire 85 allows the distal end portion 65 of extension member 76 to be formed into an angle with respect to the axis of sheath member 74. During use as a lightwand, stiffening wire 85 allows the tip to be bent at a 90 degree angle such that a glow can be more readily seen at person's suprasternal notch indicating correct placement in the trachea. The stiffening wire is of such rigidity that it will flex back such to allow its withdrawal from the endotracheal tube 34 of FIG. 13 when the extendable stylet is being retracted after successful intubation.

Figure 9:
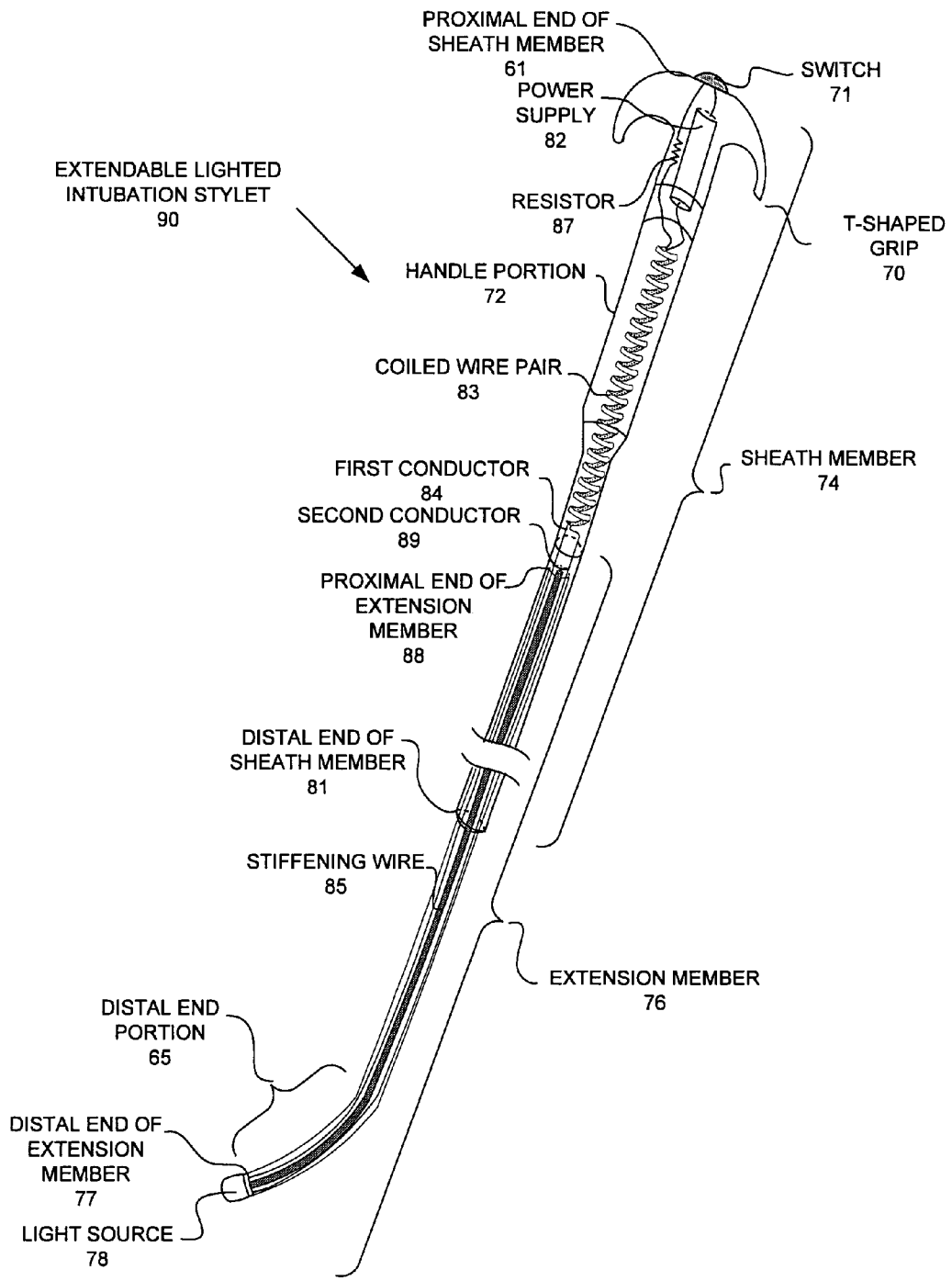
FIG. 9 is a cross sectional side elevation drawing of an extendable lighted intubation stylet. The extendable lighted intubation stylet is shown in its fully extended position.

FIG. 9 is a cross sectional side elevated view of the extendable stylet in its fully extended position. In this extended position, a coiled wire pair 83 has flexed to allow electrical connections to be maintained as an extension member 76 has been slidably extended from a sheath member 74. Friction between the outer wall of extension member 76 and inner surface of sheath member 74 is such that it will overcome the force caused by flexion of coiled wire pair 83 thus preventing inadvertent retraction of extension member 76. In other embodiments sheath member and extension member 76 each have threaded portions and are rotatably coupled such that extension member 76 must be axially rotated to telescopically extend it relative to sheath member 74. In other embodiments, the extension and retraction of extension member 76 relative to sheath member 74 is effectuated by a spring.

In its fully extended position the extension member 76 has been slidably extended from sheath member 74 such to increase the length of the extendable stylet to approximately 70 centimeters. In this configuration the device may be used similar to a bougie, wherein the light source 78 is positioned under the epiglottis and advanced until the operator feels a slight vibratory sensations or tracheal clicking thus indicating the light source is bumping the cartilaginous tracheal rings and the device is correctly positioned in the trachea. If no vibratory sensation is felt than the extendable stylet is in the esophagus and the should be removed and repositioned.

Figure 10:
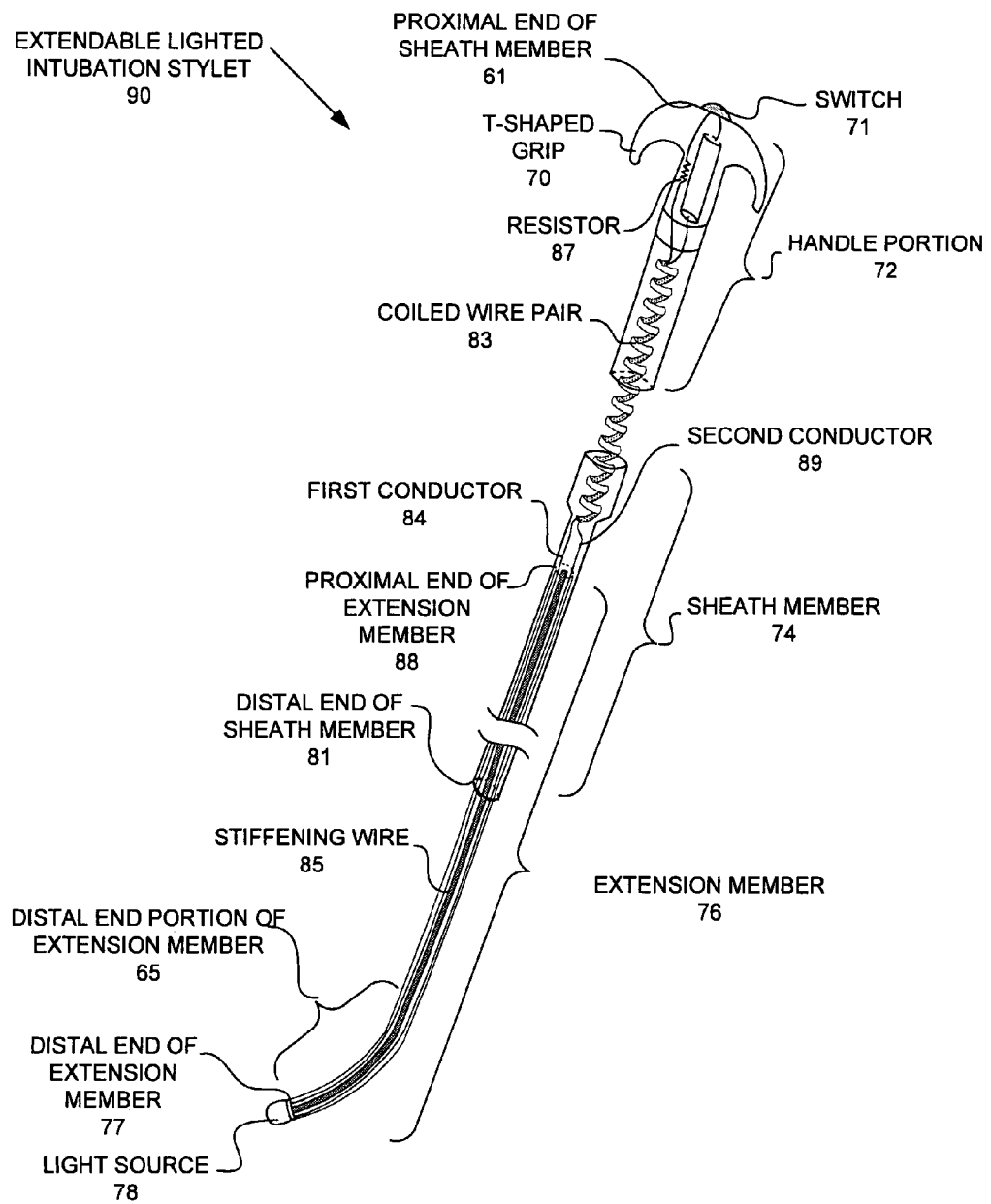
FIG. 10 is a cross sectional side elevation diagram showing displacement of handle portion of an extendable lighted intubation stylet.

FIG. 10 is an illustration showing displacement of a handle portion of an extendable lighted intubation stylet. To retract an extension member 76 relative to a sheath member 74, a handle portion 72 is pulled from sheath member 74 such to exert tension on a coiled wire pair 83 and further tension on a first conductor 84 and a second conductor 89. The force caused by removal of handle portion 72 is such to overcome the friction between the outer surface of extension member 76 and inner surface of sheath 74 thus permitting extension member 76 to slidably retract relative to sheath member 74. In some embodiments handle portion 72 and a tube section of sheath member 74 are threaded and handle portion 72 must be axially rotated with respect to tube section of sheath member 74 in order to detach handle portion 72 from the tube section of sheath member 74.

Figure 11:
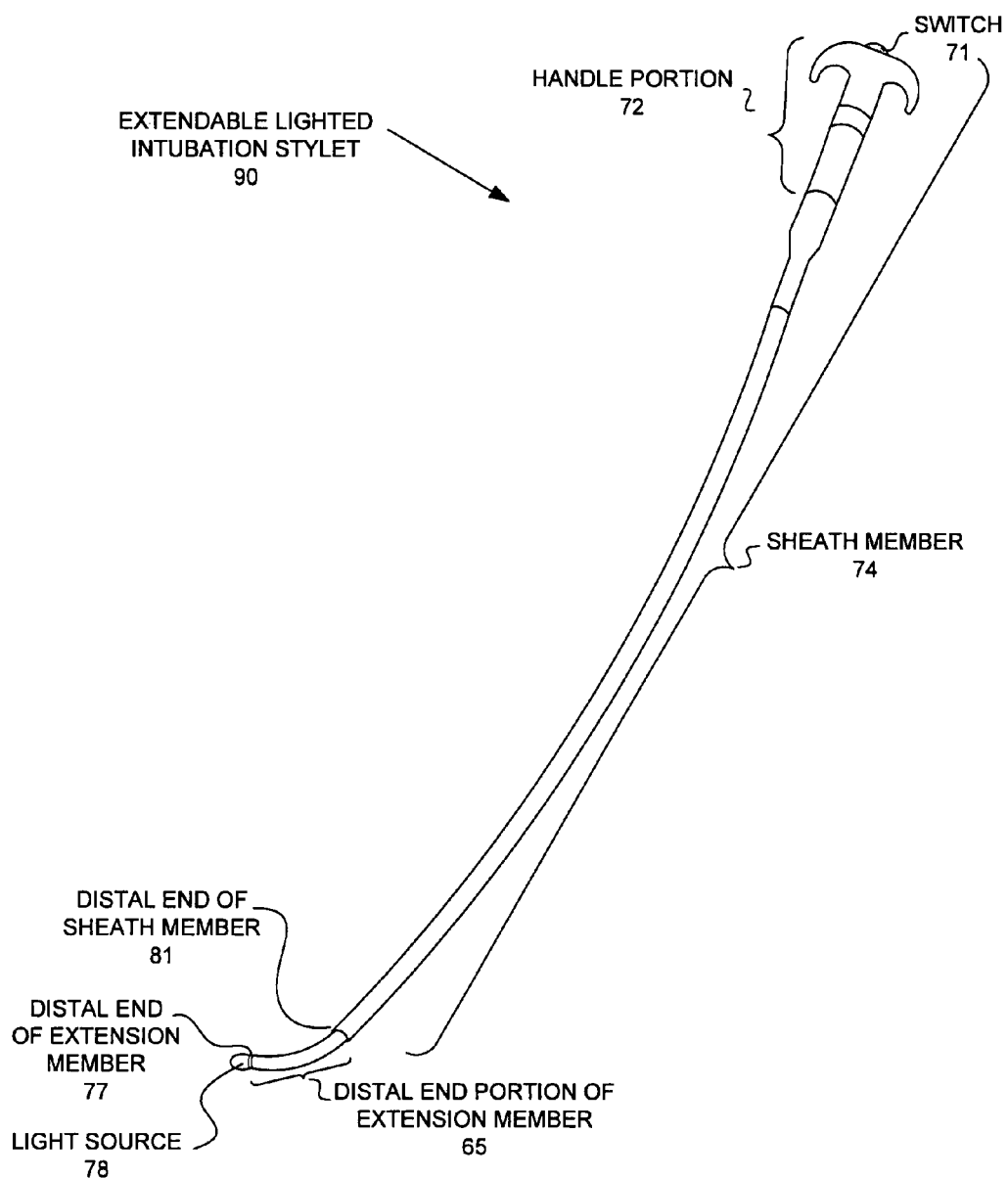
FIG. 11 is a drawing of an extendable lighted intubation stylet in its fully retracted position.

FIG. 11 is a drawing of an extendable lighted intubation stylet in accordance with one novel aspect. In this figure a light source 78 is coupled to an extension member 76 and extension member 76 is slidably coupled to a sheath member 74. The T-shaped grip of a handle portion 72 of sheath member 74 is also present in this figure. A light source 78 is controlled by a switch 71.

Figure 1:
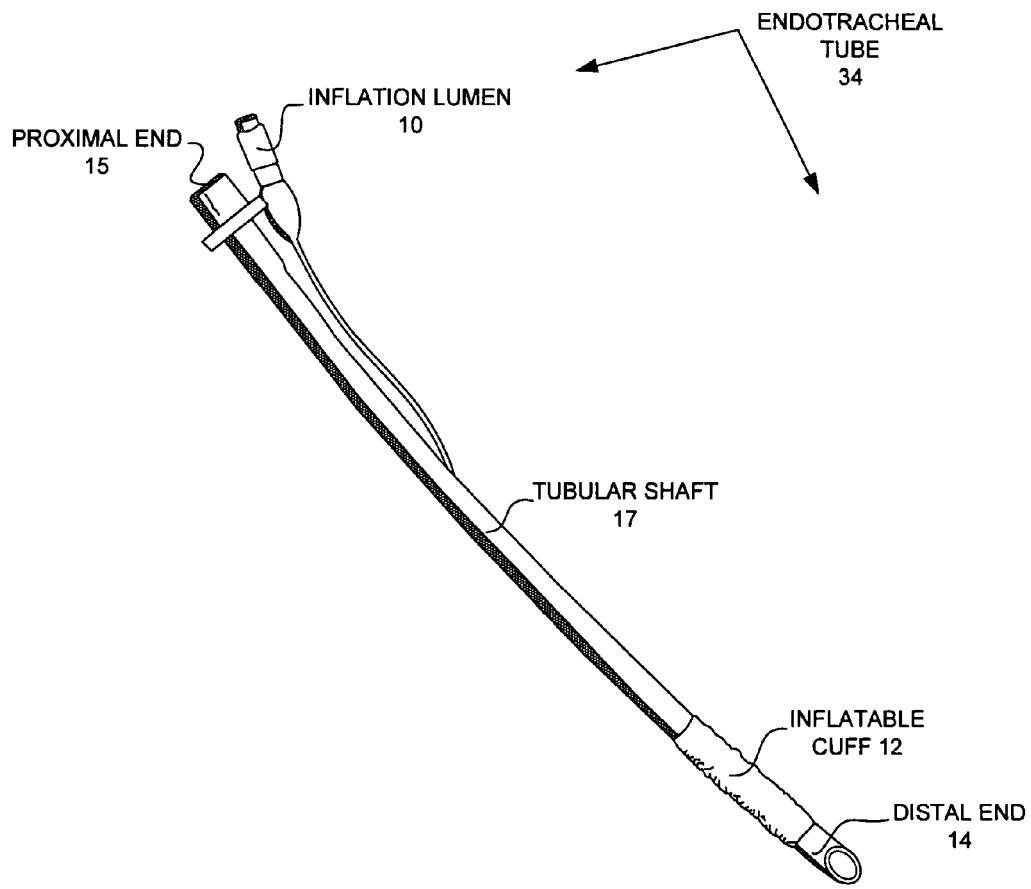
FIG. 1 is a drawing of an endotracheal tube.
Figure 2:
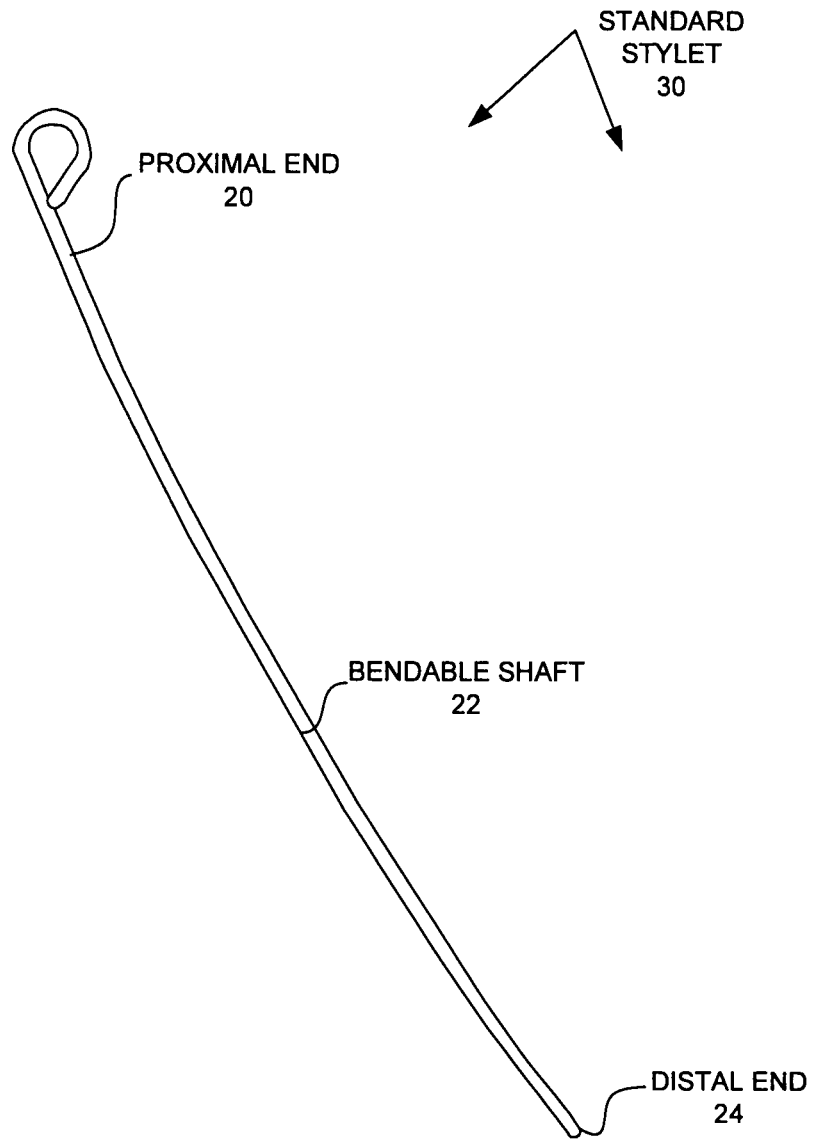
FIG. 2 is a drawing of a standard stylet.
Figure 3:
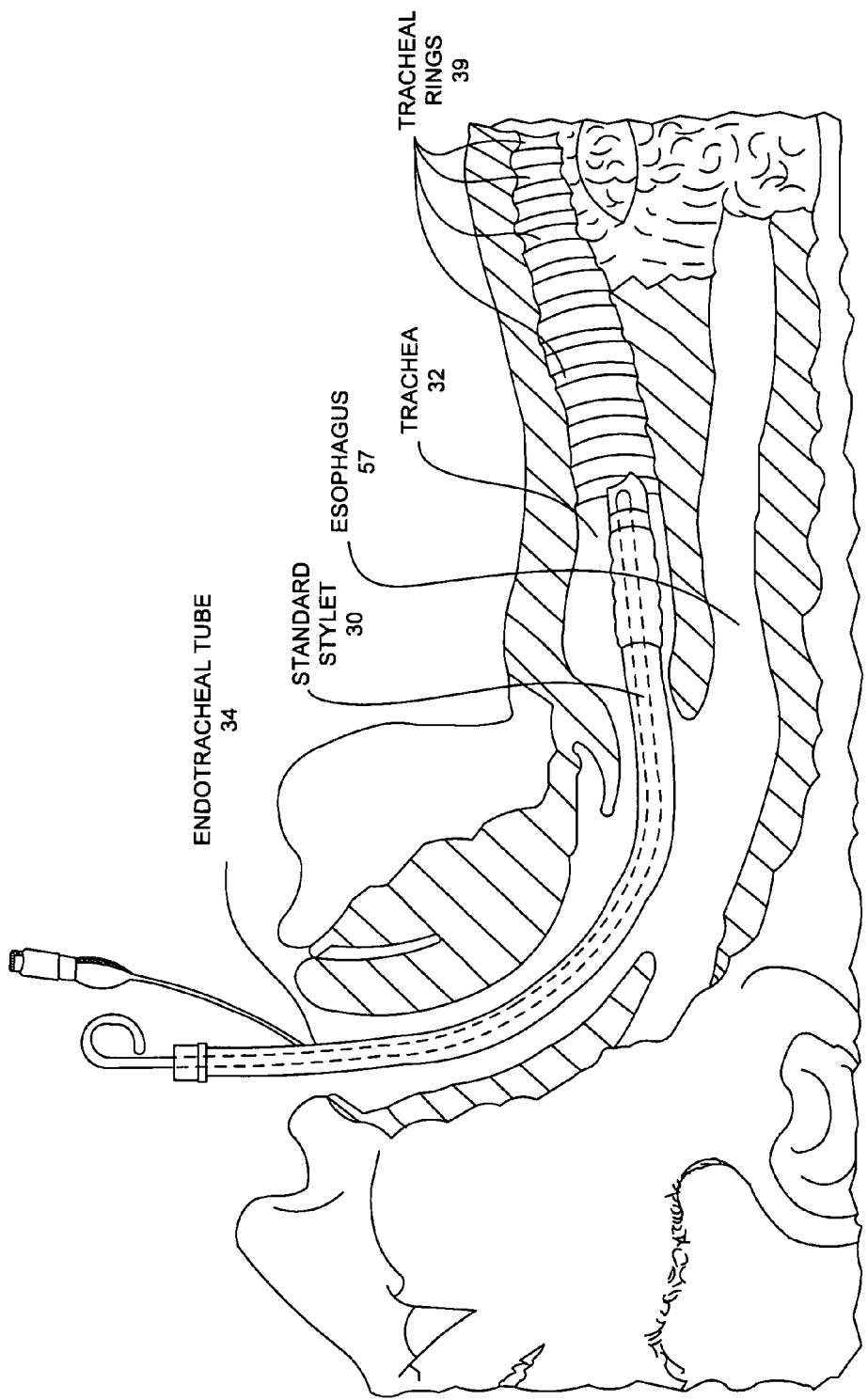
FIG. 3 is a cross sectional side elevation view of the standard stylet and endotracheal tube disposed within a person's airway.
Figure 4:
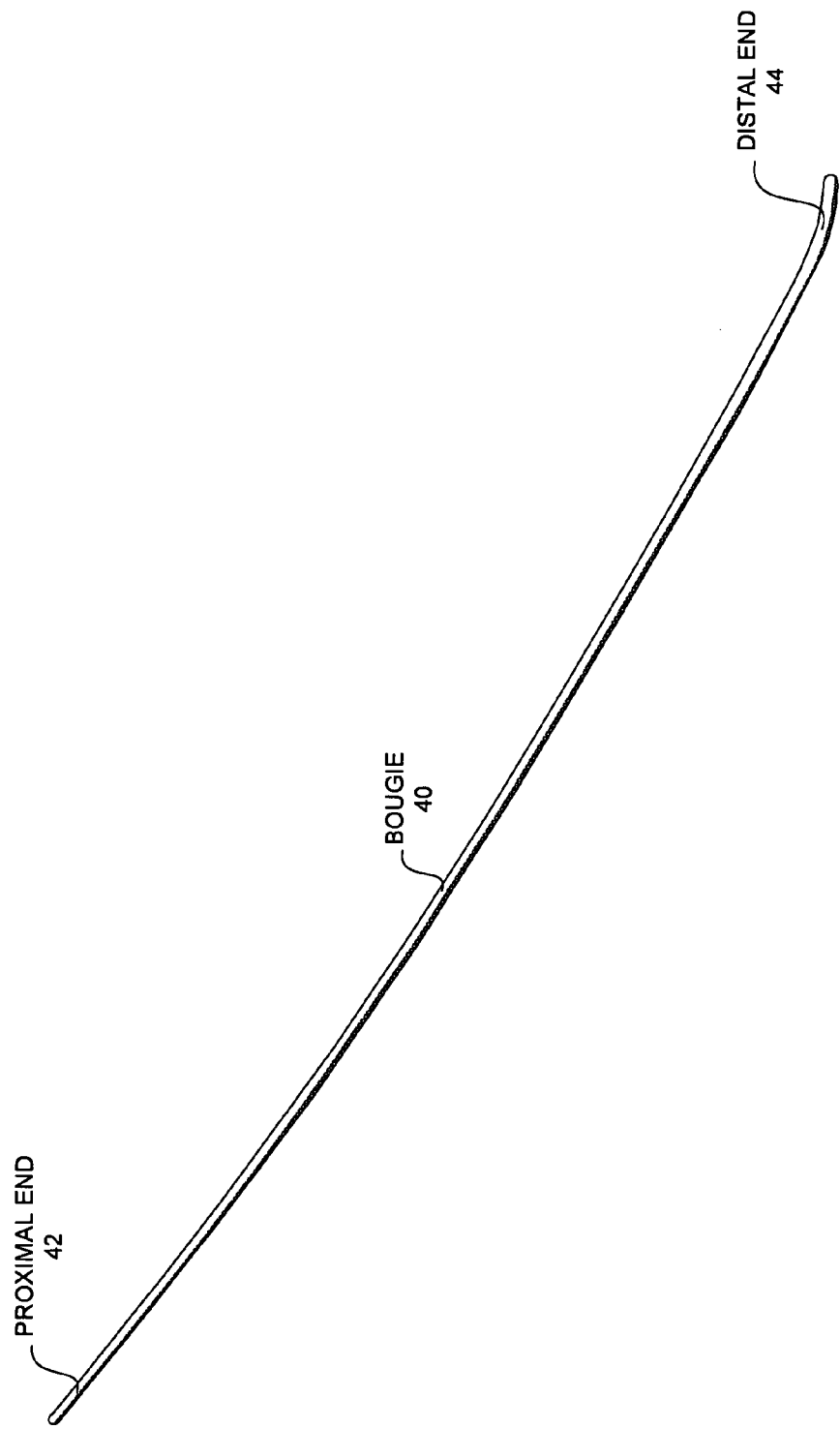
FIG. 4 is a drawing of a bougie.
Figure 5:
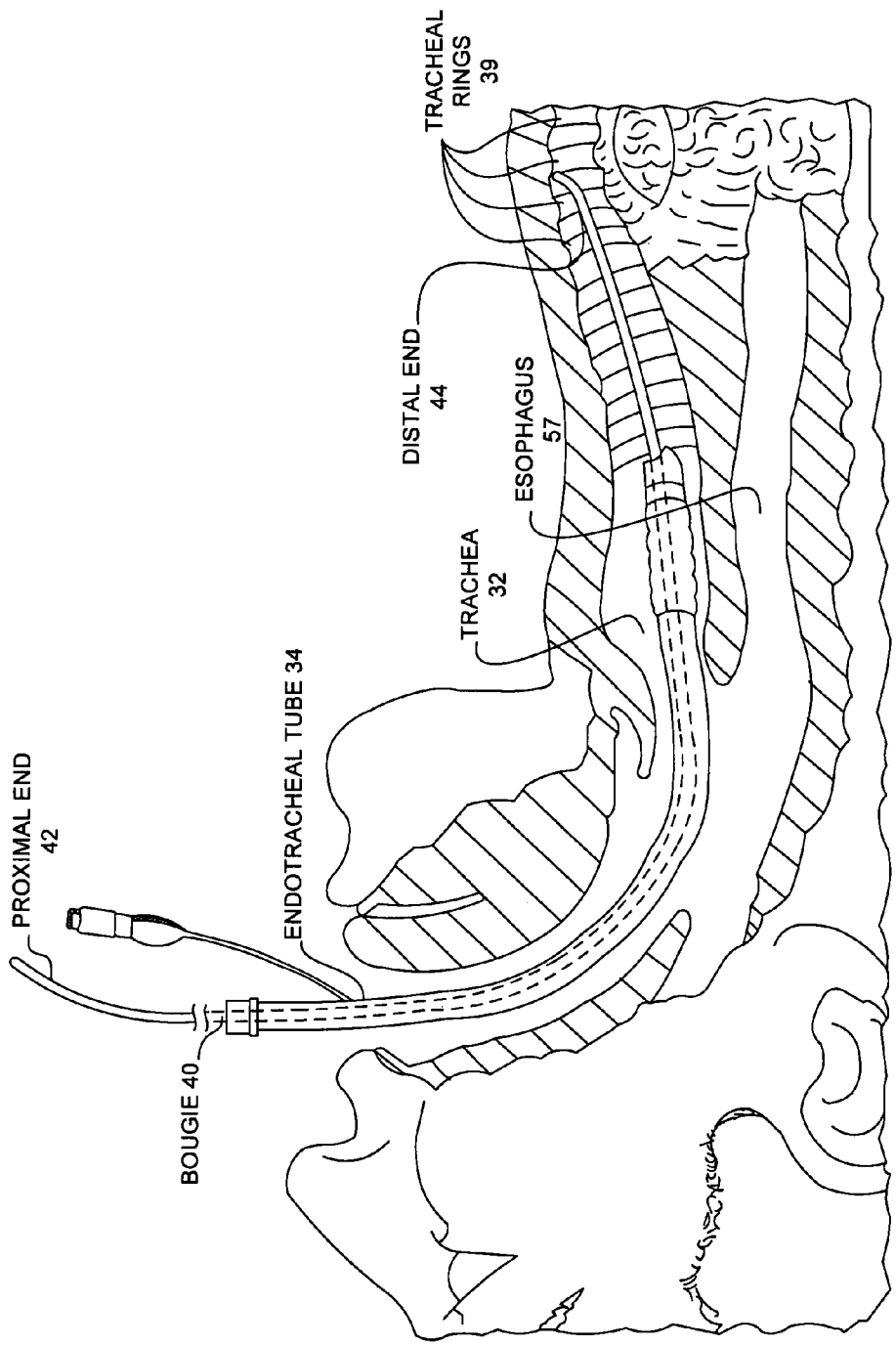
FIG. 5 is a cross sectional side elevation view of the bougie and endotracheal tube disposed within a person's airway.
Figure 6:
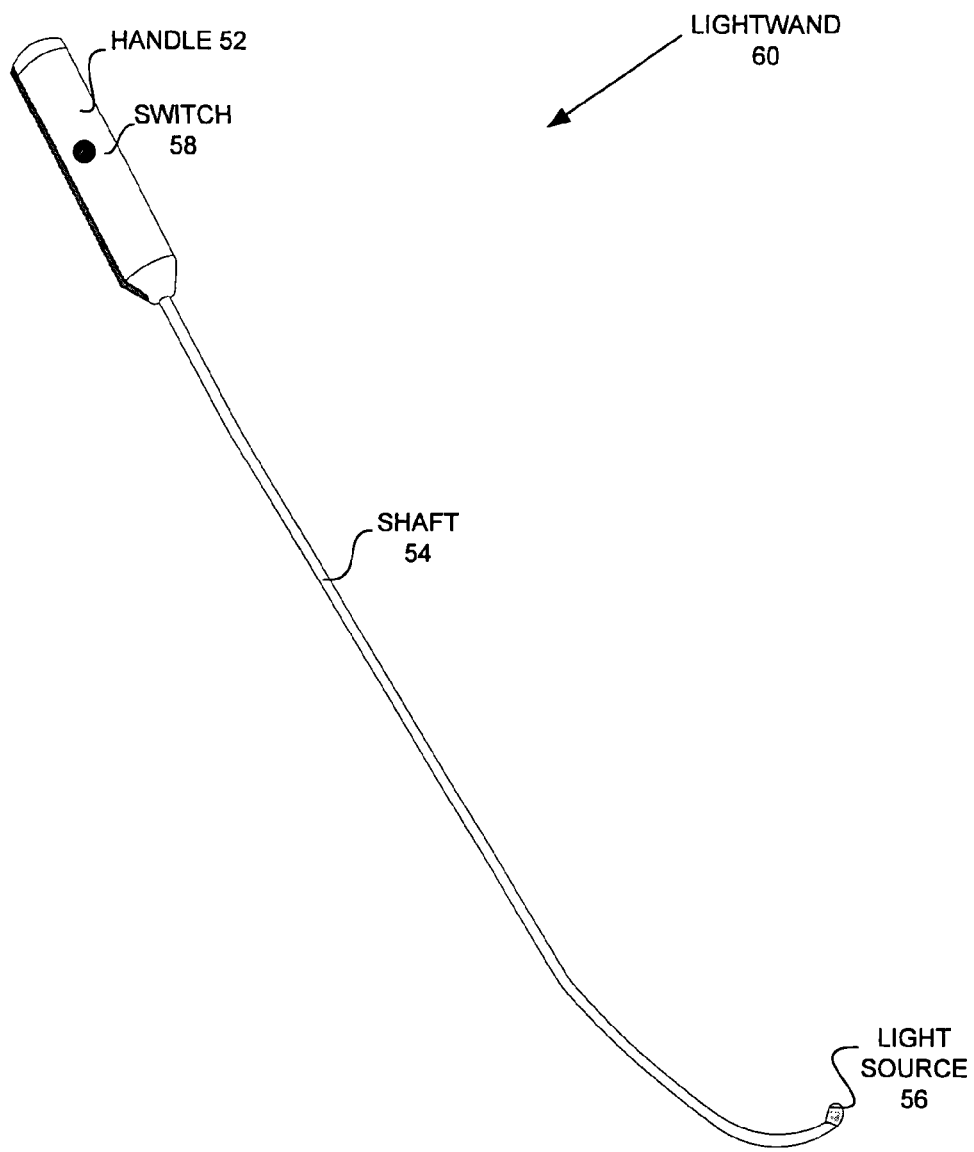
FIG. 6 is a drawing of a lightwand.
Figure 7:
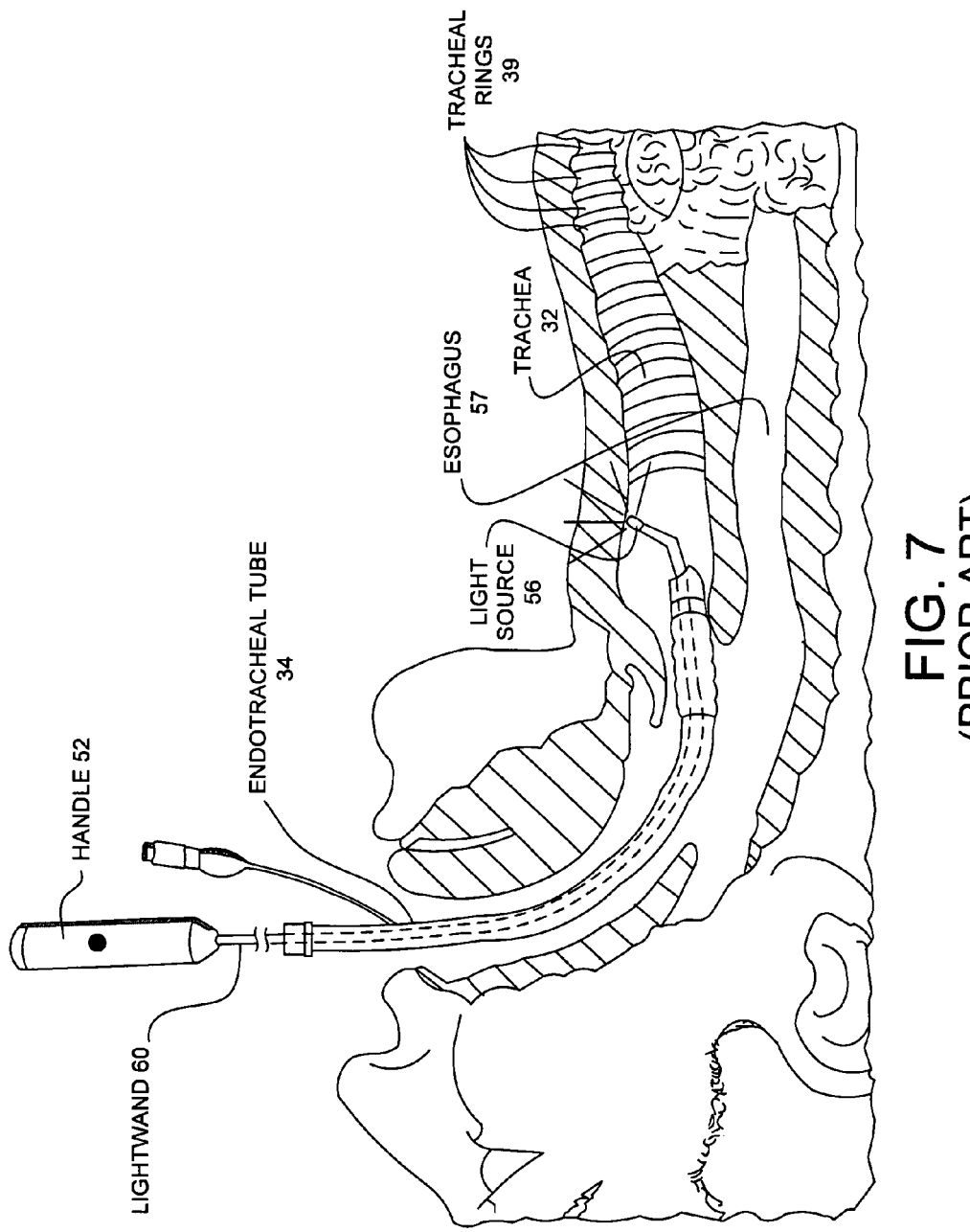
FIG. 7 is a cross sectional side elevation view of the lightwand and endotracheal tube disposed within a person's airway.

The extendable intubation stylet 90 is fully retracted in this figure and may be used in a similar fashion as a lightwand or a standard stylet. When used similar to a lightwand, an endotracheal tube is slidably mounted on sheath member 74 and a distal end portion 65 of extension member 76 is bent relative to the axis of sheath member 74. Light source 78 is switched on using switch 71 and the light source 78 and a distal end 77 of extension member 76 are inserted into the throat of a person and advanced. Light from light source 78 will be externally viewable when extendable intubation stylet is properly positioned in the airway of the person. During insertion, light from light source 78 also provides supplementary light such to aid the operator in initially locating the airway. After insertion, if light is not seen emanating from the suprasternal notch of the person, than the extendable stylet is in the person's esophagus and must be withdrawn and replaced. In its fully retracted position, extendable lighted intubation stylet 90 is also used similar to a standard stylet 30 of FIG. 2 to shape an endotracheal tube such to permit insertion into a person's airway.

In this FIG. 11, extension member 76 is fully retracted relative to sheath member 74, and in this configuration the overall length of the device is approximately 50 centimeters.

Figure 12:
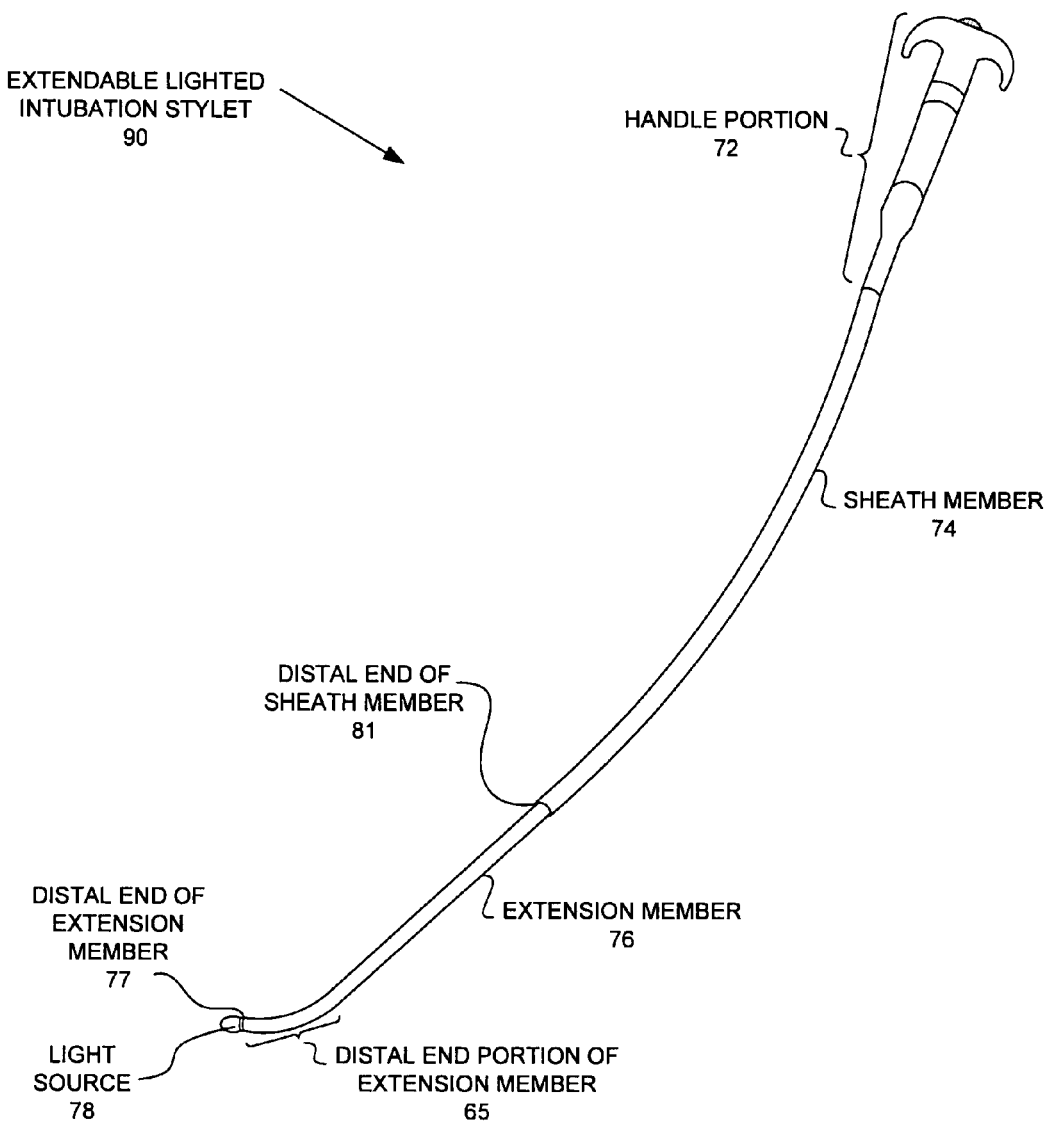
FIG. 12 is a drawing of an extendable lighted intubation stylet in its fully extended position.

FIG. 12 is a drawing of the extendable intubation stylet in its fully extended position. In this position, an extension member 76 has been slidably extended from a sheath member 74 to increase the length of the extendable stylet to approximately 70 centimeters. In this configuration the device may be operated similar to a bougie, wherein a light source 78 is positioned under the epiglottis of a person and advanced until the operator feels a slight vibratory sensation indicating that the device is correctly positioned in the trachea. If no vibratory sensation or tracheal clicking is felt, the extendable intubation stylet is in the esophagus and must be removed and repositioned. In some embodiments light source 78 will be controlled by a switch 71 of FIG. 11 such that it may remain on when extendable intubation stylet is extended position. In those embodiments, when the extendable intubation stylet is extended and light source 78 is on, light will be seen emanating from the suprasternal notch of the person similar to a lightwand. This provides additional validation, in addition to the tracheal clicking, that the extendable intubation stylet is correctly positioned in the person's airway.

Figure 13:
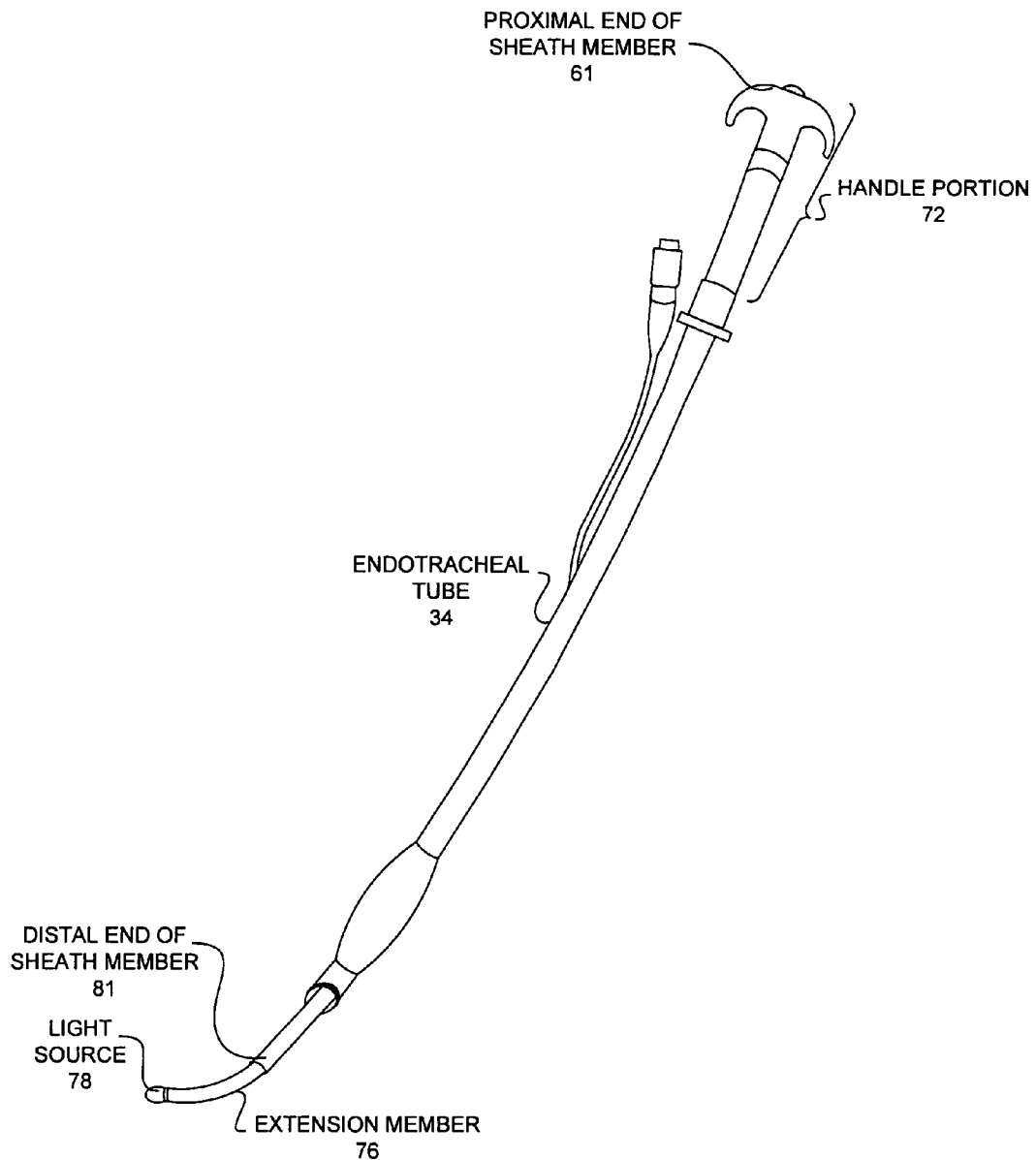
FIG. 13 is a drawing of an endotracheal tube mounted upon an extendable lighted intubation stylet in its fully retracted position.

FIG. 13 shows an endotracheal tube 34 disposed upon an extendable stylet. To mount an endotracheal tube 34 onto the extendable stylet, the endotracheal tube is slidably moved over a light source 78, over an extension member 76, and a sheath member 74 until it abuts a handle portion 72. In this figure, the extendable stylet is shown in its fully retracted position. Once the extendable intubation stylet is correctly positioned in the airway of a person, endotracheal tube 34 may be held in place while the extendable stylet is slidably removed from the person, leaving the endotracheal tube disposed within the trachea. Oxygen and/or anesthetics may then be applied to the person via endotracheal tube 34.

Figure 14:
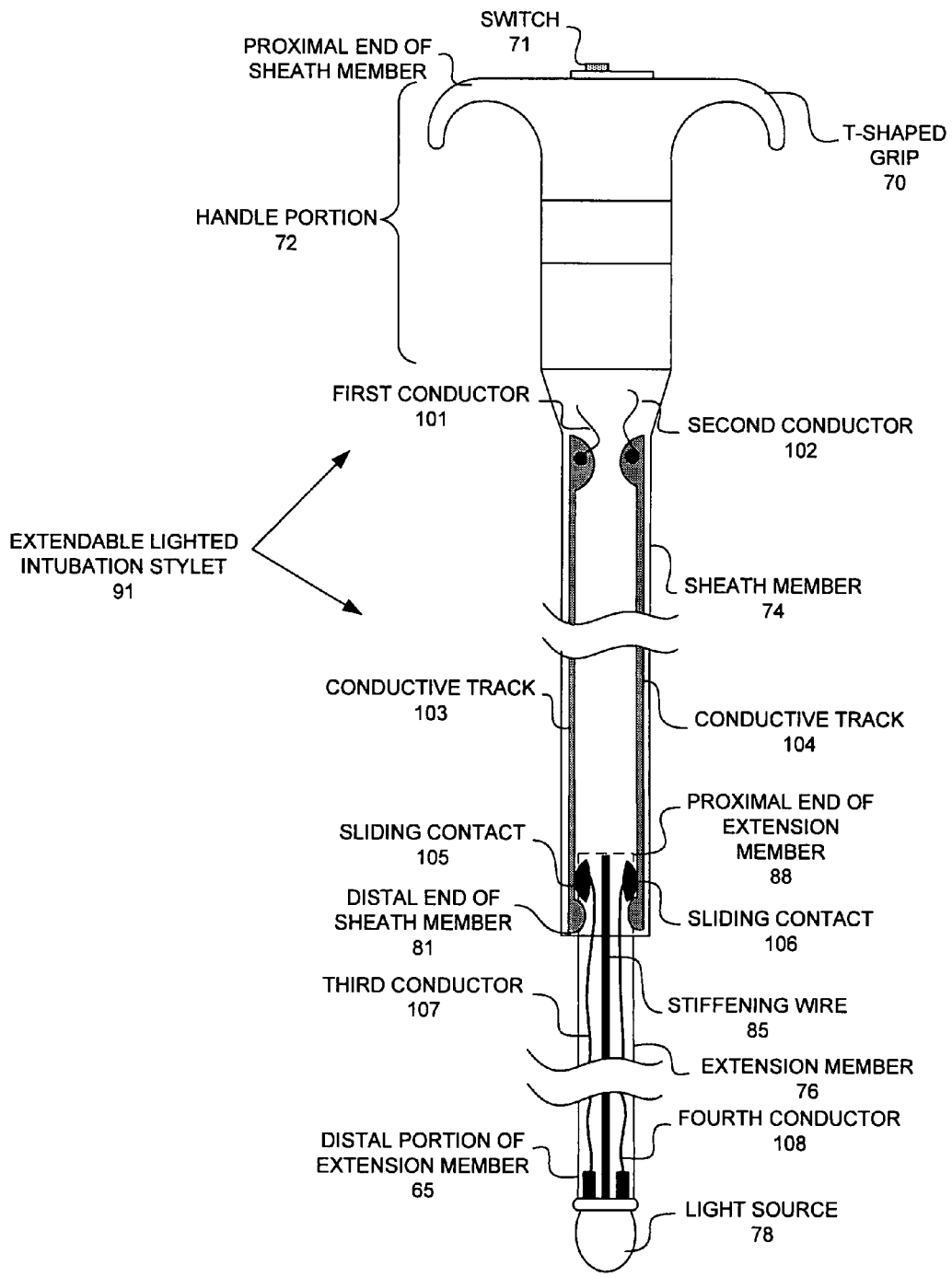
FIG. 14 is a cross sectional side elevation diagram of another embodiment of an extendable lighted intubation stylet with conductive tracks disposed along the inner aspect of the sheath member.

FIG. 14 is another embodiment of an extendable lighted intubation stylet 91 which obviates the need for the coiled wire pair 83 of FIG. 8. In FIG. 14, a first conductor 101 connects to a terminal of resistor 87 of FIG. 8. The opposite end of first conductor 101 is connected to a conductive track 103 which is disposed along an inner surface of a sheath member 74. A sliding contact 105 is conductive and is slidably coupled to conductive track 103. A third conductor 107 further connects sliding contact 105 to one terminal of a light source 78. The opposite terminal of light source 78 is connected to a fourth conductor 108 shown disposed within an extension member 76. At a proximal end 88 of extension member 76, fourth conductor 108 is connected to a sliding contact 106 which is conductive and is slidably coupled to a conductive track 104 which is disposed along the interior surface of sheath member 74. The opposite end of conductive track 104 is connected to the negative terminal of power supply 82 of FIG. 8.

In this embodiment of FIG. 14, extension member 76 can be slidably extended and retracted relative to sheath member 74 while still maintaining electrical connectivity such to permit electrical control of light source 78. Conductive tracks 103 and 104 can be metal tracks or can be alternatively constructed of electroconductive tape or similar material.

Figure 15:
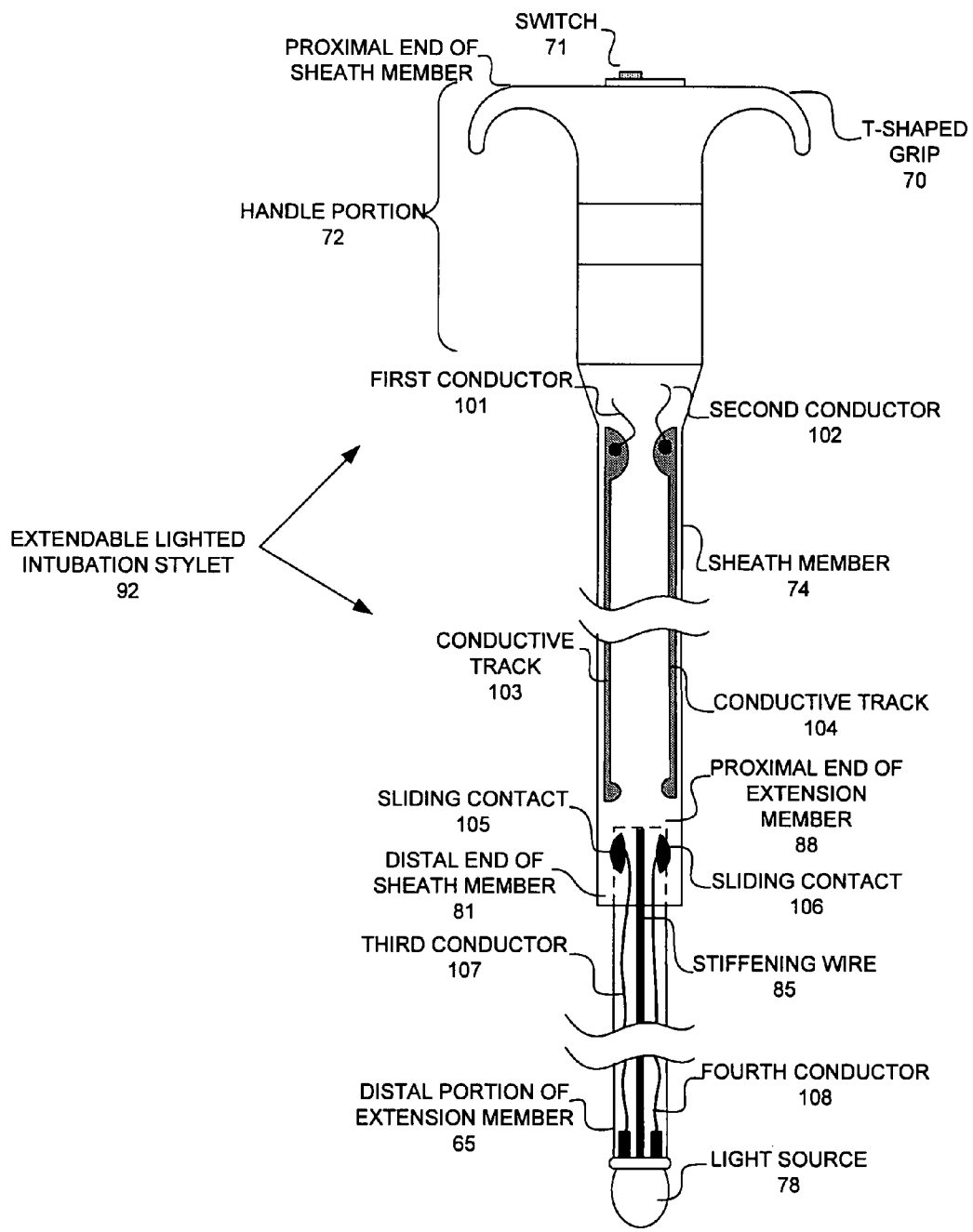
FIG. 15 is a cross sectional side elevation diagram of another embodiment of an extendable lighted intubation stylet with conductive tracks only partially disposed along the inner aspect of the sheath member.

FIG. 15 displays yet another embodiment of an extendable lighted intubation stylet 92. In this embodiment, a conductive track 103 and a conductive track 104 do not extend the entire length of a sheath member 74 thus permitting a light source 78 to be electrically controlled when the extendable lighted intubation stylet 92 is in its fully retracted position. When the extendable lighted intubation stylet 92 is in the fully extended position, electrical connectivity to light source 78 is not maintained and light source 78 will be electrically disabled. In this embodiment, the extendable stylet may be used similar to a lightwand when it is in its fully retracted position and similar to a bougie when it is extended. In yet another embodiment, conductive tracks 103 and 104 make electrical contact with sliding contacts 105 and 106 only when the extendable stylet is in its fully retracted position and light source 78 will not turn on if extendable stylet is extended from its fully retracted position.

Figure 16:
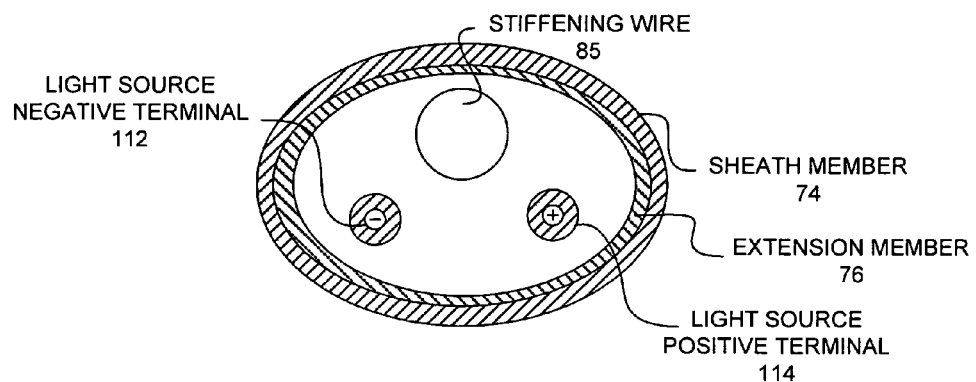
FIG. 16 is a cross sectional drawing of an extendable lighted intubation stylet.

FIG. 16 is a cross sectional diagram of an extendable lighted intubation stylet. FIG. 16 displays a sheath member 74, an extension member 76, a stiffening wire 85, a light source positive terminal 114 and a light source negative terminal 112. In order to control distal end portion 65 of extension member 76 of FIG. 8, and to prevent it from inadvertently rotating and becoming a source of trauma, both sheath member 74 and extension member 76 are oval in shape. This oval construction prevents extension member 76 from rotating within sheath member 74 and potentially causing trauma to the person.

Figure 17:
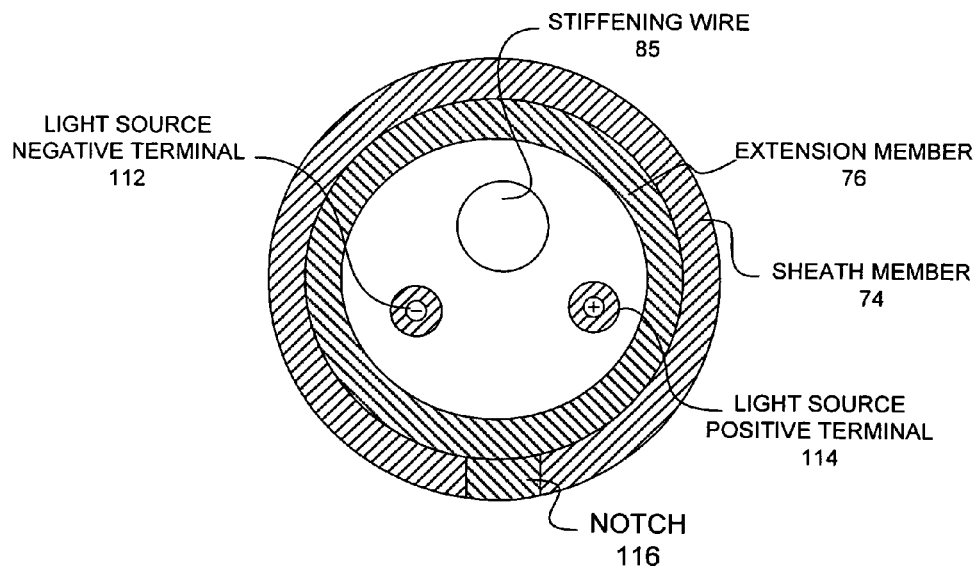
FIG. 17 is a cross sectional drawing of another embodiment of an extendable lighted intubation stylet.

A cross sectional diagram of one alternative embodiment is shown in FIG. 17. FIG. 17 displays a sheath member 74, an extension member 76, a stiffening wire 85, a light source positive terminal 114, a light source negative terminal 112 and a notch 116. In order to control the distal end portion 65 of extension member 76 of FIG. 8, and to prevent it from inadvertently rotating and becoming a source of trauma, sheath member 74 has notch 116 which is filled by a corresponding raised section disposed upon the outside surface of extension member 76. The notch 116 thus prevents extension member 76 from axially rotating relative to sheath member 74 thereby reducing the possibility of trauma from inadvertant rotation.

Figure 18:
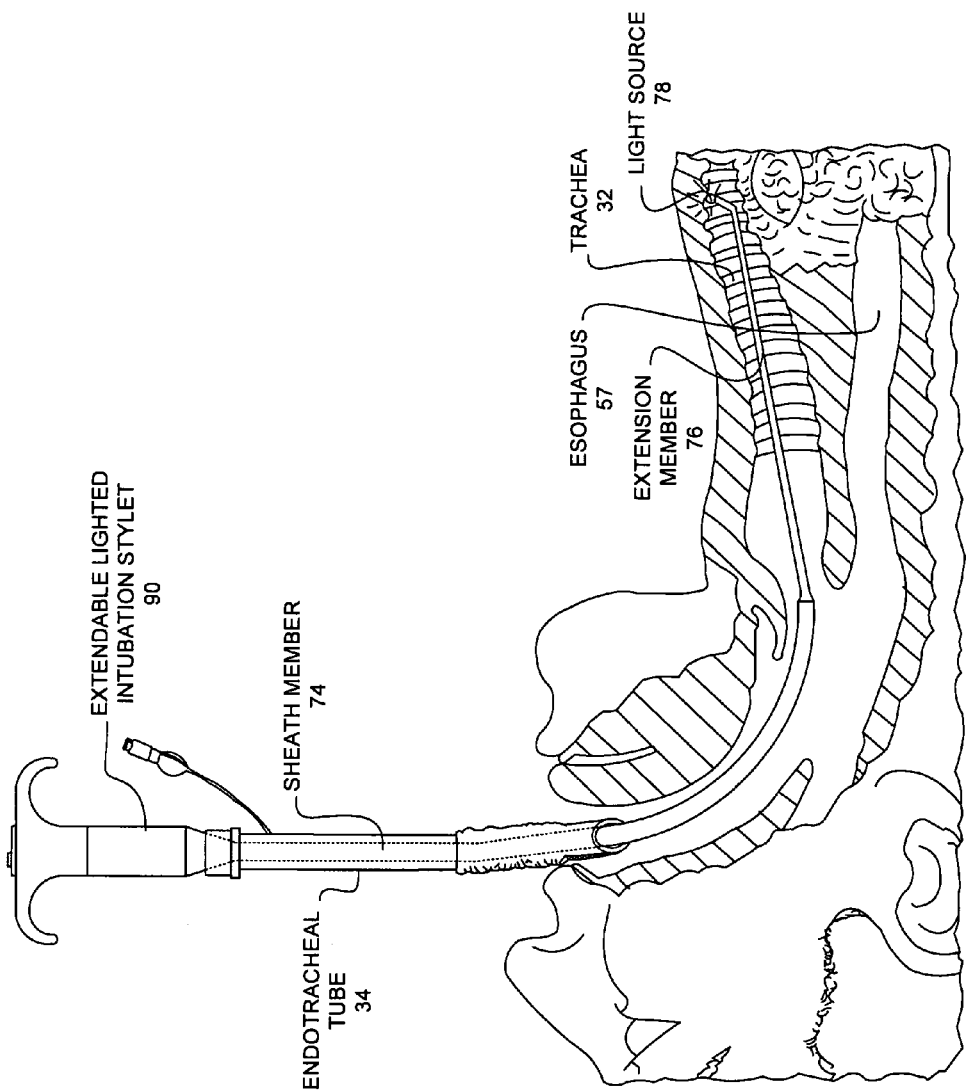
FIG. 18 is a cross sectional side elevation diagram showing an extendable lighted intubation stylet and endotracheal tube in extended position, the endotracheal tube has not yet been advanced into the airway of a person.

FIG. 18 shows an extendable lighted intubation stylet and endotracheal tube 34 before the endotracheal tube 34 is slidably positioned within person. The extendable lighted intubation stylet is shown with an extension member 76 fully extended relative to sheath member 74. In this manner, when the extendable lighted intubation stylet is advanced into a trachea 32, light from a light source 78 can be seen emanating from the suprasternal notch of a person indicating correct placement. Additionally, the operator will also feel vibratory sensations or tracheal clicking at the handle portion of the extendable intubation stylet as it is further advanced and the distal portion of extension member 76 bumps the cartilaginous rings located in the person's trachea 32. In this manner the operator has two sources of verification that they have correctly placed the extendable stylet into the person's trachea. Once correct placement has been validated, the endotracheal tube can be slidably moved along the a sheath member 74 towards an extension member 76 into the person using the extendable stylet as a guide. Once the endotracheal tube 34 is properly positioned in the person's trachea, the extendable stylet could then be withdrawn leaving endotrachial tube 34 in place for administration of oxygen or anesthetics.

Figure 19:
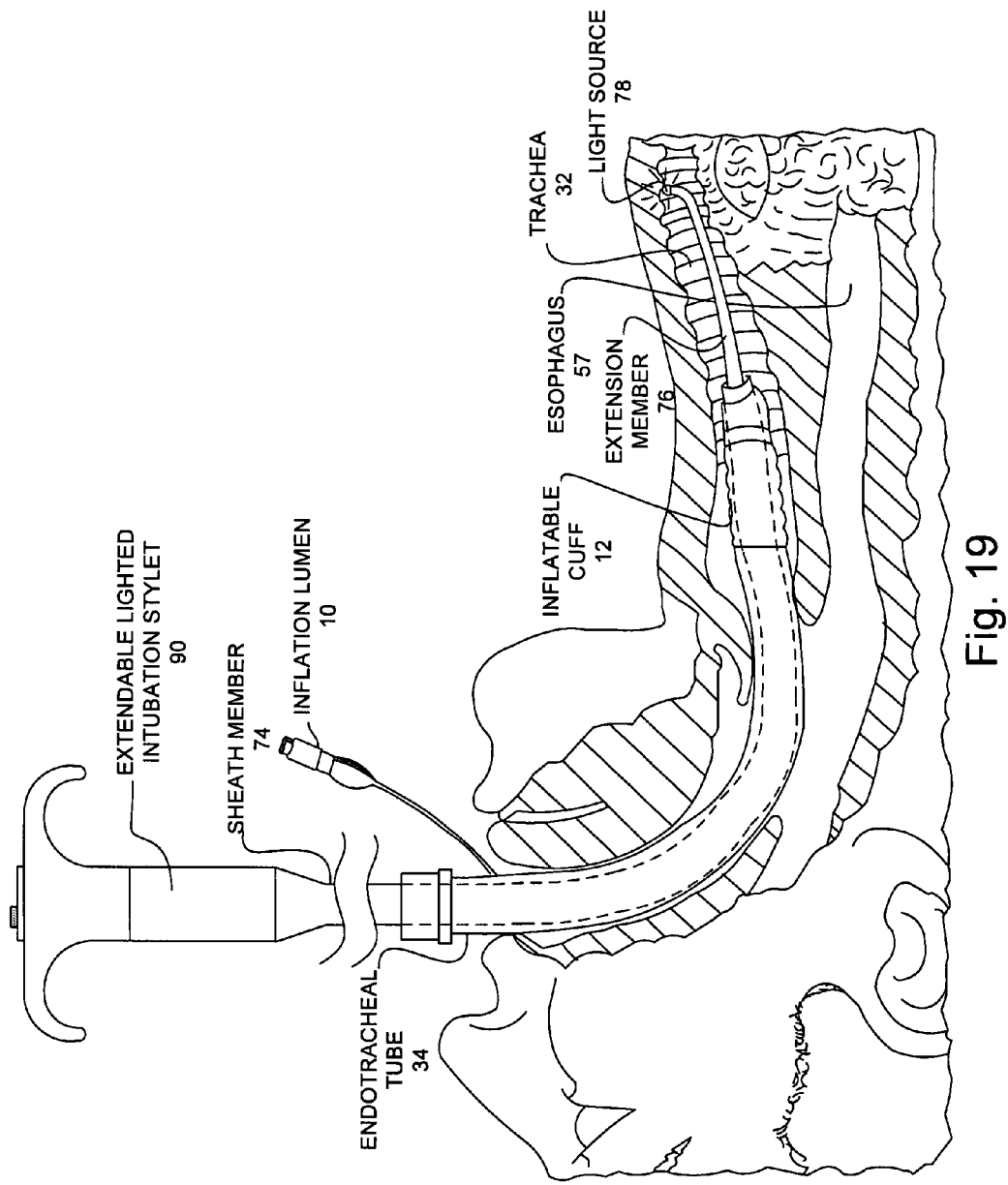
FIG. 19 is a cross sectional side elevation diagram showing an extendable lighted intubation stylet in its fully extended position with an endotracheal tube disposed within a person's trachea.

FIG. 19 is a drawing showing extendable lighted intubation stylet 90 and endotracheal tube 34 disposed within a person. Extendable lighted intubation stylet is shown with an extension member 76 in a fully extended position.

Figure 20:
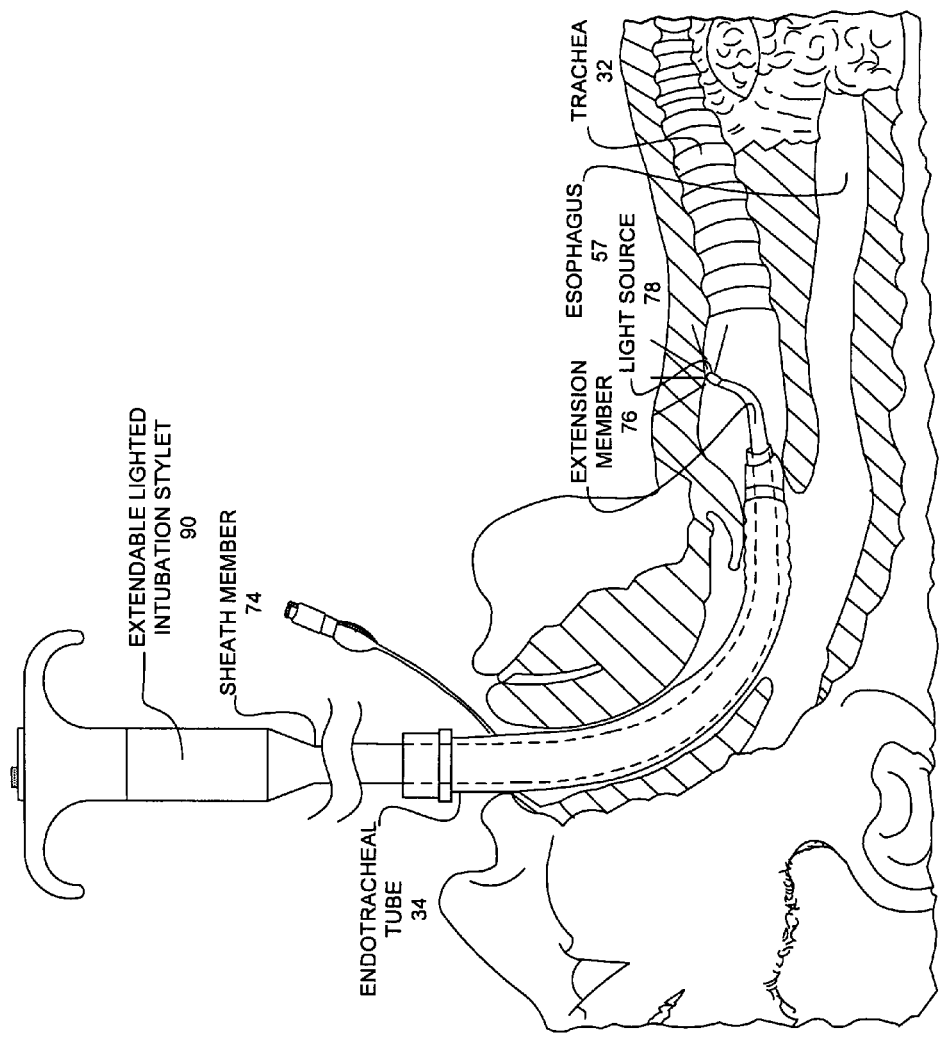
FIG. 20 is a cross sectional side elevation diagram showing an extendable lighted intubation stylet in its fully retracted position and an endotracheal tube disposed within a person's airway.

FIG. 20 is a drawing showing an extendable lighted intubation stylet 90 and endotracheal tube 34 disposed within a person's airway. In this drawing, light from a light source 78 is emanating from the person and is viewable externally at the suprasternal notch of the person. In this figure, the extendable lighted intubation stylet 90 is properly positioned in the airway and extends into a trachea 32 of a person. The light from light source 78 permits the operator to validate that the extendable lighted stylet is in the airway and is not disposed in an esophagus 57.

Figure 21:
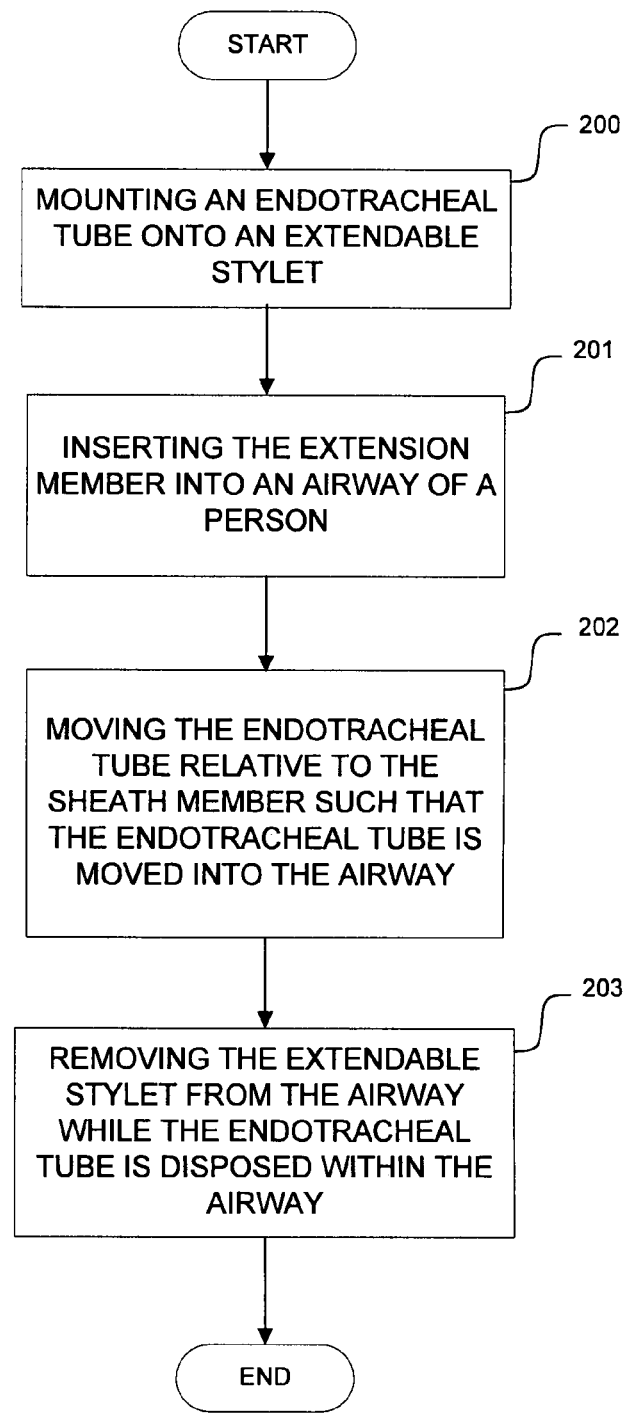
FIG. 21 is a flowchart of a novel method of using an extendable stylet to intubate a person.

FIG. 21 is a simplified flowchart diagram of a novel method in accordance with one embodiment. In the initial step 200, an endotracheal tube 34 is mounted onto an extendable lighted intubation stylet. FIG. 13 shows an endotracheal tube 34 disposed upon the extendable stylet. To mount endotracheal tube 34 onto the extendable stylet, endotracheal tube 34 is slidably moved over light source 78, over extension member 76, and a sheath member 74 until it abuts handle portion 72.

Next, in step 201, the extension member 76 of FIG. 13 is inserted into the airway of a person. The light source 78 and extension member of FIG. 13 are slipped underneath the person's epiglottis and slidably advanced through the airway and into the trachea. The light source 78 may be on and externally viewable to the operator through the suprasternal notch of the person. This is one method of verifying that the extension member 76 is correctly positioned in the airway. Additionally, tracheal clicking can also be felt at handle portion 72 of proximal end 61 of sheath member 74 of FIG. 13 when extension member 76 is further advanced into the airway of a person. This further validates that the extendable stylet has been properly inserted into the trachea rather than in the person's esophagus. FIG. 18 shows the extendable lighted intubation stylet after extension member 76 has been advanced through the airway and into the trachea 32. The endotracheal tube 34 is disposed upon the sheath member 74 of extendable lighted intubation stylet 90 of FIG. 18.

In a third step 202, the endotracheal tube is moved relative to the sheath member such that the endotracheal tube is moved into the trachea. FIG. 19 shows the endotracheal tube 34 after it has been slidably advanced along sheath member 74 of the extendable lighted intubation stylet 90 and into the trachea of a person. During intubation, endotracheal tube 34 is slidably moved along sheath member 74 in a direction towards extension member 76. The extendable intubation stylet guides endotracheal tube 34 into its proper position in the trachea. Once properly in place, the inflation lumen 10 may be used to inflate inflatable cuff 12 thus securing the endotracheal tube 34 within the person's trachea.

In the fourth step, 203, the extendable lighted intubation stylet is removed from the mouth while the endotracheal tube remains disposed within the trachea of the person. Once the extendable intubation stylet has been removed, the person is successfully intubated and oxygen or anesthetics can be applied to the person via the endotracheal tube 34 of FIG. 20.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. An apparatus comprising:
   a sheath member having a proximal end and a distal end, the sheath member having a length in a range of forty centimeters to sixty centimeters, the sheath member having an outside diameter of less than seven millimeters:
   an extension member having a proximal end and a distal end, the extension member being slidably mounted relative to the sheath member so that the distal end of the extension member telescopes from the distal end of the sheath member, the extension member having a length in a range of ten centimeters to forty centimeters, wherein the extension member has a distal end portion that is relatively more bendable than a distal end portion of the sheath member: and
   a Light Emitting Diode (LED) disposed upon the distal end portion of the extension member: wherein the sheath member includes a first conductive track and a second conductive track, wherein the extension member includes a first sliding contact and a second sliding contact, and wherein the first sliding contact slidably engages the first conductive track as the extension member is extended from the sheath member.

2. The apparatus of claim 1, wherein the first sliding contact does not engage the first conductive track if the extension member is fully extended with respect to the sheath member.

* * * * *